US007988951B2

(12) United States Patent
Edelson

(10) Patent No.: US 7,988,951 B2
(45) Date of Patent: Aug. 2, 2011

(54) METHOD FOR INDUCING SELECTIVELY SUPPRESSED IMMUNE RESPONSE TO TRANSPLANTED TISSUE OR CELLS

(75) Inventor: Richard Leslie Edelson, Westport, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 12/627,920

(22) Filed: Nov. 30, 2009

(65) Prior Publication Data

US 2010/0183735 A1 Jul. 22, 2010

Related U.S. Application Data

(62) Division of application No. 10/217,856, filed on Aug. 13, 2002, now Pat. No. 7,625,557.

(60) Provisional application No. 60/312,004, filed on Aug. 13, 2001.

(51) Int. Cl.
*A01N 1/02* (2006.01)
*A61M 37/00* (2006.01)
*C12N 5/08* (2006.01)

(52) U.S. Cl. ................... 424/9.81; 424/93.7; 424/93.71; 435/2; 604/4.01; 604/6.03; 604/6.08

(58) Field of Classification Search .................. None
See application file for complete search history.

(56) References Cited

U.S. PATENT DOCUMENTS

| 4,321,918 | A | 3/1982 | Clark, II |
| 4,683,889 | A | 8/1987 | Edelson |
| 4,838,852 | A | 6/1989 | Edelson et al. |
| 6,194,204 | B1 | 2/2001 | Crawford et al. |
| 6,524,855 | B2 | 2/2003 | Edelson et al. |
| 6,596,275 | B1 | 7/2003 | Bartholeyns et al. |
| 6,602,709 | B1 | 8/2003 | Albert et al. |
| 6,800,300 | B1 | 10/2004 | Miller et al. |
| 2002/0051771 | A1 | 5/2002 | Bolton et al. |
| 2002/0114793 | A1 | 8/2002 | Edelson et al. |
| 2003/0133914 | A1 | 7/2003 | Edelson et al. |
| 2005/0084966 | A1 | 4/2005 | Edelson et al. |

FOREIGN PATENT DOCUMENTS

| WO | 97/34472 | 9/1997 |
| WO | 00/62818 | 10/2000 |

OTHER PUBLICATIONS

Greinix, et al. Successful Use of Extracorporeal Photochemotherapy in the Treatment of Severe Acute and Chronic Graft-Versus-Host Disease, Blood, vol. 92, No. 9, 1998, pp. 3098-3104.*
Greinix, et al. Extracorporeal Photochemotherapy in the Treatment of Severe Steroid-Refractory Acute Graft-Versus-Host Disease: A Pilot Study, Blood, vol. 96, No. 7,, 2000, pp. 2426-2431.*
Ullrich, Photoinactivation of T-cell function with psoralen and UVA radiation suppresses the induction of experimenta; murine graft-versus-host disease across major histocompatibility barriers: Jour. Invest. Dermatol., vol. 96, No. 3, 1991, pp. 303-308.*
Cohen, et al. CD4+CD25+ Immunoregulatory T Cells: New Therapeutics for Graft-Versus-Host Disease, The Rockefeller University Press, vol. 196, No. 3, Aug. 5, 2002, pp. 401-406.
Chambers, The expanding world of co-stimulation: the two-signal model revised, Trends in Immunology, vol. 22, No. 4, Apr. 2001, pp. 217-223.
Hoffmann, et al. Donor-type CD4+CD25+ Regulatory T Cells Suppress Lethal Acute Graft-Versus-Host Disease after Allogeneic Bone Marrow Transplantation, The Rockefeller University Press, vol. 196, No. 3, Aug. 5, 2002, pp. 389-399.
Rossi, M. et al., Plasmacytoid Dendritic Cells: Do They Have a Role in Immune Responses After Hematopoietic Cell Transplantation? Human Immunology Dec. 2002, vol. 63, No. 12, pp. 1194-1200.
Heshmati, F. Mechanisms of Action of Extracorporeal Photochemotherapy Transfusion and Apheresis Science Aug. 2003, vol. 29, No. 1, pp. 61-70, Abstract.
Ying G et al: "Tricyclic antidepressants prevent the differentiation of monocytes into macrophage-like cells in vitro." Cel Biol Toxicol 2002; 18(6):425-37.
Beaudoin L et al: "NKT cells inhibit the onset of diabetes by impairing the development of pathogenic T cells specific for pancreatic beta cells." Immunity. Dec. 2002; 17(6):725-36.
Kitazawa T et al: "Studies on delayed systemic effects of ultraviolet B radiation on the induction of contact hypersensitivity, 3. Dendritic cells from secondary lymphoid organs are deficient in interleukin-12 production and capacity to promote activation and differentiation of T helper type 1 cells." Immunology. Feb. 2000;99(2):296-304.
Tang A et al: "Inhibition of epidermal Langerhans cell function by law dose ultraviolet B radiation. Ultraviolet B radiation selectively modulates ICAM-1 (CD54) expression by murine Langerhans cells." J Immunol. May 15, 1991;146(10):3347-55.
Shen W et al: "Ganglioside GD1a impedes lipopolysaccharide-induced maturation of human dendritic cells." Cell Immunol. Dec. 2002;220(2):125-33.

(Continued)

*Primary Examiner* — David A Saunders
(74) *Attorney, Agent, or Firm* — McCarter & English, LLP

(57) ABSTRACT

Transimmunization methods incorporating skin immunologic challenges are described for either selectively suppressing the immune response of recipients of transplanted tissue or cells or monitoring induced anti-cancer immunity. In one embodiment, skin from the transplant donor is allografted to the transplant recipient to induce an immunological response to the transplanted skin. A quantity of blood is taken from the recipient and treated to render the T cells in the blood apoptotic and to induce differentiation of blood monocytes into dendritic cells. The treated blood is incubated and administered to the recipient to induce formation of suppressor T cell clones which reduce the number of T cells attacking the transplanted tissue or organ. This tolerogenic approach can be complemented by also feeding the immature dendritic cells apoptotic or necrotic cells from the organ donor. In a second embodiment, dendritic cells loaded with tumor antigens are injected intradermally to monitor the anti-cancer immunity induced by Transimmunization.

9 Claims, No Drawings

OTHER PUBLICATIONS

Lateef Z et al: "Orf virus-encoded interleukin-10 inhibits maturation, antigen presentation and migration of murine dendritic cells." J Gen Virol. May 2003;84(Pt5): 1101-0.

Shurin MR et al: "Inhibition of CD40 expression and CD-40-mediated dentritic dell function by tumor-derived IL-10." Int J Cancer. Sep. 1, 2002;101(1):61-8.

Semnani RT et al: "Filarial antigens impair the function of human dendritic cells during differentiation." Infect Immun. Sep. 2001;69(9):5313-22.

Chung F: "Anti-inflammatory cytokines in asthma and allergy: interleukin-10, interleukin-12, interferon-gamma." Mediators Inflamm. Apr. 2001;10(2):51-9. Links.

Hackstein H et al: "Aspirin inhibits in vitro maturation and in vivo immunostimulatory function of murine myeloid dendritic cells." J Immunol. Jun. 15, 2001;166(12):7053-62.

Komi J et al: "Non-steroidal anti-oestrogens inhibit the differentiation of synovial macrophages into dendritic cells." Rheumatology (Oxford). Feb. 2001;40(2):185-91.

Moore KW et al: "Interleukin-10 and the interleukin-10 receptor." Annu Rev Immunol. 2001;19:683-785.

Bernstein SH et al: "A randomized phase II study of BB-10010: a variant of human macrophage inflammatory protein-1 alpha for patients receiving high-dose etoposide and cyclophosphamide for malignant lymphoma and breast cancer." BR J Haematol. Dec. 1997;99(4):888-95.

Askenase PW et al: "Gamma delta T cells in normal spleen assist immunized alpha beta T cells in the adoptive cell transfer of contact sensitivity. Effect of Bordetella pertussis, cyclophosphamide, and antibodies to determinants on suppressor cells." J Immunol. Apr. 15, 1995;154(8):3644-53.

De Smedt T et al: "Effect of interleukin-10 on dendritic cell maturation and function." Eur J Immunol. May 1997;27(5):1229-35.

Hirohata S: "Suppression of human B cell responsiveness by CD4+ T cells does not involve CD95-CD95 ligand interactions." Cell Immunol. Nov. 1, 1997;181(2):182-91.

Estry DW et al: "A comparison of the fibrinogen receptor distribution on adherent platelets using bath soluble fibrinogen and fibrinogen immobilized on gold beads." Eur J Cell Biol. Apr. 1991;54(2):196-210.

Blank K et al: "Self-immobilizing recombinant antibody fragments for immunoaffinity chromatography: generic, parallel, and scalable protein purification." Protein Expr Purif. Mar. 2002;24(2):313-22.

Garlie NK et al: "T cells activated in vitro as immunotherapy for renal cell carcinoma: characterization of 2 effector T-cell populations." J Urol. Jul. 2001;166(1):299-303.

Foger N et al: "CD44 supports T cell proliferation and apoptosis by apposition of protein kinases." Eur J Immunol Oct. 2000;30(10):2888-99.

Hanau D et al: "A method for the rapid isolation of human epidermal Langerhans cells using immunomagnetic microspheres." J Invest Dermatol. Sep. 1988;91(3):274-9.

Thomas R et al: "Human peripheral blood dendritic cell subsets. Isolation and characterization of precursor and mature antigen-presenting cells." J. Immunol. Nov. 1, 1994;153(9):4016-28.

Yanagihara S et al: "EBI1/CCR7 Is a New Member of Dendritic Cell Chemokine Receptor That is Up-Regulated Upon Maturation." The Journal of Immunology 1998, 161: 3096-3102.

Li B et al: "Pretreatment of recipients with mitomycin-C-treated dendritic cells induces significant prolongation of cardiac allograft survival in mice." Transplantation Proceedings vol. 34, Issue 8, Dec. 2002, pp. 3426-3428.

Hawiger D et al: "Dendritic Cells Induce Peripheral T Cell Unresponsiveness Under Steady State Conditions in Vivo," The Journal of Experimental Medicine, vol. 194, No. 5, Sep. 17, 2001, 769-780.

Jiga L et al: "Generation of tolerogenic dendritic cells by treatment with mitomycin c: inhibition of allogeneic T-cell response is mediated by downregulation of ICAM-1, CD80, and CD86." Transplantation. vol. 77(11), Jun. 15, 2004, pp. 1761-1764.

Tanigawa T et al: "Injection of mitomycin-C-treated spleen cells induces donor-specific unresponsiveness to cardiac allografts in rats [experimental transplantation]." Transplantation. vol. 67(5), Mar. 15, 1999, pp. 653-658.

Albert M et al: "Immature Dendritic Cells Phagocytose Apoptotic Cells via $\alpha v\beta 5$ and CD36, and Cross-present Antigens to Cytotoxic T Lumphocytes" J. Exp. Med. vol. 188, No. 7, Oct. 5, 1998 1359-1368.

Morel A et al: "Regulation of major histocompatability complex case II synthesis by interleukin-10." Immunology 2002 106 229-236.

Kakumu S et al: "Decreased function of peripheral blood dendritic cells in patients with hepatocellular carcinoma with hepatitis B and C virus infection." Journal of Gastroenterology and Hepatology, 2000 15, 31-436.

Coates P et al: "Human myeloid dendritic cells transduced with an adenoviral interleukin-10 gene construct inhibit human skin graft rejection in humanized NOD-scid chimeric mice." Gene Therapy, 2001 8, 1224-1233.

Corintis S et al: "Regulatory Activity of Autocrine IL-10 on Dendritic Cell Functions." J Immunol. 2001, 166: 4312-4318.

Griffin M et al: "Dendritic cell modulation by $1\alpha,25$ dihydroxyvitamin D3 and its analogs: A vitamin D receptor-dependent pathway that promotes a persistent state of immaturity in vitro and in vivo." PNAS Jun. 5, 2001 vol. 98, No. 12, 6800-6805.

Canning M et al: "$1\alpha,25$-Dydroxyvitamin D3 (1,25(OH)2D3) hampers the maturation of fully active immature dendritic cells from monocytes." European Journal of Endocrinology 2001 145 351-357.

Shurin MR et al: "Inhibition of CD40 expression and CD-40 mediated dendritic cell function by tumor-derived IL-10." Int J Cancer Sep. 1, 2002;101(1):61-68.

Simon JC et al: "UVB-Irradiated Dendritic Cells Induce Nonproliferating, Regulatory Type T Cells." Skin Pharmacol Appl Skin Physiol 2002:15:330-334.

Fay, et al, Dendritic cell immunotherapy of metastatic melanoma using CD34+ hemotopietic progenitor-derived dendritic cells (CD34-DC) induced immune responses to melanoma antigen and resulted in clinical regression of metastatic disease, Blood, Nov. 16, 2000, vol. 96, p. 807a.

PCT/US02/25703 International Preliminary Examination Report, dated May 10, 2005.

Russell-Jones, R. "Shedding Light on Photphersis", The Lancet. Mar. 17, 2001, vol. 357, pp. 820-821.

Barr, et al., "Photopheresis for the Prevention of Rejection in Cardiac Transplantation", The New England Journal of Medicine, 1998, pp. 1744-1751.

Yarmane, et al., "Suppression of Anti-Skin-Allograft Response by Photodamages Effector Cells—The Modulating Effects of Prednisolone and Cyclophosphamide", Transplantation. 1992, pp. 119-124.

Perez, "Induction of a Cell-Transferable Suppression of Alloreactivity by Photodamages Lymphocytes", Transplantation, 1992, pp. 896-903.

Perez, "DNA Associated with the Cell Membrane is Involved in the Inhibition of the Skin Rejection Response in the Inhibition of the Skin Rejection Response Induced by Infusions of Photodamaged Alloreactive Cells that Mediate Rejection of Skin Allograft", Photochemistry and Photobiology, vol. 55, No. 6, 1992, pp. 839-849.

Oliven et al: "Extracorporeal Photopheresis: a review", Blood Reviews, vol. 15, Jun. 2001, pp. 103-108.

Rook et al: Photopheresis: Clinical application and Mechanism of Actions:, Journal of Investigative Dermatology Symposium Proceedings, vol. 4, nr. 1, Sep. 1999 pp. 85-90.

Kanada et al: "Photopheresis Monocytes Produce Cytokines that Induce Monocyte-to-Dendritic Cell Maturation During Overnight Incubation", Journal of Investigative Dermatology, vol. 117, nr. 2, May 12, 2001 p. 535, abstract 873.

Berger et al: "Induction of Tumor-Loaded Dendritic Cells", Int J Cancer, vol. 91, Feb. 15, 2001, pp. 438-447.

European Communication dated Dec. 22, 2006 for application No. 02 750 482.6-1222.

Brooks, CG. "The effects of cell density, incubation temperature, syngeneic serum, and syngeneic red blood cells on mouse lymphocyte responses in vitro", J Immunol Methods, Dec. 9, 1975 (2): 171-84, abstract.

Purrott, R.J. et al.; Cellular and Molecular Life Sciences; vol. 37, No. 4, Apr. 1981; pp. 407-408; abstract.

\* cited by examiner

METHOD FOR INDUCING SELECTIVELY SUPPRESSED IMMUNE RESPONSE TO TRANSPLANTED TISSUE OR CELLS

PRIOR APPLICATIONS

This application is a divisional application of U.S. patent application Ser. No. 10/217,856 filed on Aug. 13, 2002, now U.S. Pat. No. 7,625,557, the entire contents of which are incorporated herein by reference, which claims the benefit of U.S. Provisional Application No. 60/312,004, filed on Aug. 13, 2001.

FIELD OF THE INVENTION

The present invention is directed to methods of manipulating skin to increase the safety and efficacy of tissue or organ transplants or to assess and permit improved titration of anti-cancer immunotherapy. In a first embodiment, skin allografts are placed on a prospective organ transplant recipient. The skin allografts induce a simulation of the immune rejection of the planned organ transplant which normally occurs when individuals receive transplanted organs or tissue, such as bone marrow or stem cells, from genetically different individuals. This skin-simulated rejection, followed by a process referred to herein as Transimmunization, permits the recipient's immune system to become trained to accept tissue from the prospective donor. In a second embodiment, tumor-loaded dendritic cells, simulating antigenic tumor cells, are introduced into the dermis of the cancer patient to induce local anti-tumor T cell responses, which then permit assessment and therapeutic titration of the level of anti-tumor immunity induced by Transimmunization.

In the transplantation situation, allografted skin is used in concert with a procedure referred to as Transimmunization to prolong the survival in recipients of transplanted organs or tissue, such as bone marrow, stem cells, or skin, donated from genetically distinct individuals. Transimmunization is a process whereby blood monocytes are induced to differentiate into dendritic cells, and the induced dendritic cells can then be loaded with tissue antigens. In certain circumstances, in which the antigens are distinctive of cancers, the loaded dendritic cells can be used to "vaccinate" or immunize the patient against the cancer cells. In other situations, in which the patient is the intended recipient of a transplanted organ, the loaded dendritic cells can be used to suppress the immuno-logic reactions otherwise capable of causing rejection of the transplanted organ.

In the present invention, the dendritic cells phagocytize anti-graft T cells from a potential transplant recipient. These anti-graft T cells are induced in the potential transplant recipient as a result of an allograft of skin from the potential transplant donor. Since the allografted skin contains the same transplantation antigens which typify the potential transplanted organ, the anti-graft T cells induced by the small skin allograft are precisely those which would naturally be induced by the actual organ transplant. The dendritic cells, loaded with antigens from the anti-graft T cells, are infused into the potential transplant recipient leading to an immuno-logical response that suppresses the activity of anti-graft T cells. This immunological response to the clones of the induced T cells can reduce the capacity of anti-graft T cells in the organ transplant recipient to attack and damage the transplanted organ. Because of their small size and the simplicity of transplanting them, additional skin allografts can be placed, prior to transplantation of the larger prospective organ, to determine when the patient has been properly prepared to receive the prospective organ. When the transplanted small skin allograft is immunologically tolerated (not acutely rejected) by the prospective organ recipient, the patient will have been effectively prepared to receive the planned organ transplant.

In a modification of this invention, apoptotic or necrotic cells from the donor can be fed to the recipient's immature dendritic cells, to enhance the recipient's immunologic tolerance of the transplanted organ. Immature dendritic cells, displaying on their surface antigens distinctive of the donor's tissues, are capable of suppressing the activity of all anti-allograft T cell clones. Therefore, feeding cells (e.g., leukocytes or cultured cells of any type) from the donor to immature dendritic cells of the recipient and then reinfusing those antigen-loaded immature dendritic cells can contribute greatly to immunologic tolerance of the allograft. This variation of Transimmunization can be used independently or in concert with the T cell loading method described above.

In another embodiment of the present invention, autologous tumor-loaded dendritic cells are used for skin testing to assess the level of immunity achieved via Transimmunization against an individual patient's malignant cells. The tumor-loaded dendritic cells can also serve the complementary purposes of augmenting the desirable anti-tumor immunity induced in these patients by Transimmunization.

BACKGROUND OF THE INVENTION

Transplantation of organs, tissue or cells from one genetically distinct person (donor) to another (recipient) is hindered by the recipient's immunologic rejection of the donated organs or cells. This rejection phenomenon is understood to involve both cellular and humoral mechanisms, mediated respectively by T cells and antibodies. The recipient's immune system targets distinguishing histocompatibility antigens on the transplanted cells. Except in rare cases, the donor's histocompatibility antigens will not match exactly the recipient's histocompatibility antigens, and the recipient's immune system attacks the incompatible donor organs or cells.

With respect to immunologically mediated rejection, the most potent of the histocompatibility antigens are the major histocompatibility complexes (MHC) known as the human leukocyte antigens, HLA-A, HLA-B and HLA-C. Although originally defined by their presence on the cell membranes of human leukocytes, they have long been recognized to be present on virtually all of the nucleated cells of the human body. Since each person receives genes encoding one set of these antigens from each parent, human cells typically express six major HLA antigens. In addition to the major histocompatibility antigens, there are several minor histocompatibility antigens.

When tissue or cells are transplanted, it is desirable to match, to the maximum extent possible, the histocompatibility antigens of the donor and the recipient. The best immunologic match between donor and recipient is between identical twins, since they share the same six major HLA antigens. In addition, identical twins also share the same minor histocompatibility antigens, and therefore organs or cells transplanted from one identical twin to the other are immunologically tolerated. In the far more common situation in which the donor and recipient are not genetically identical, some level of immunologic rejection of transplanted tissue regularly occurs. To minimize this rejection and permit survival of the engrafted tissue, efforts are routinely made to find the best match between donor and recipient. If an identical twin is not available, the next best choice is typically a non-identical sibling of the recipient sharing the same six major HLA antigens, a situation which occurs on the average in one out of four siblings. Such a six out of six HLA match between siblings is preferable to a six out of six match between unrelated individuals, because the matched siblings will also more likely share at least some minor histocompatibility antigens inherited from their common parents. Yet, because they are not identical siblings, there is a high probability of some difference in the minor histocompatibility antigens, and the donor and recipient will almost certainly be sufficiently distinct in terms of cellular antigens that some level of rejection will occur following transplantation of tissue from one sibling to another.

The adverse reactions following transplantation of an organ or tissue from one genetically distinct individual to another can be profoundly dangerous. The primary adverse reaction is immunologic rejection of the transplanted organ or tissue. If the organ is life-sustaining, such as a heart, liver or lung, the destruction of that organ may lead directly to the death of the patient. In other circumstances, such as rejection of insulin producing pancreatic islet cells or kidneys, the quality of life of the recipient may be devastated by the tissue rejection. In order to prevent or limit the rejection, patients typically receive a combination of immunosuppressive drugs, which introduce their own major side effects. These drugs are usually globally immunosuppressive, thereby greatly increasing the susceptibility of the recipient to serious infections, often by organisms against which an uncompromised immune system would readily defend. The individual immunosuppressive drugs each have their own set of other adverse effects, especially when used in the dosages necessary to inhibit rejection of transplanted organs. For example, high doses of prednisone precipitate diabetes mellitus and hypertension, while simultaneously causing demineralization of supporting bones. Another commonly used immunosuppressive drug, cyclosporine A, has major toxic effects on the kidney. Globally immunosuppressive treatments also increase the susceptibility of transplant recipients to opportunistic infections, against which normal individuals have strong defenses.

These adverse effects have stimulated searches for therapies that can more selectively suppress the rejection of transplanted tissue, while leaving the remainder of the immune system intact and not injuring other important organs. An especially promising approach has been the use of a conventional Photopheresis device to deliver the immunotherapy referred to herein as "Transimmunization" to prevent or reverse rejection of transplanted organs. Depending on the circumstances, the therapeutic impact of the Transimmunization can be enhanced by following the conventional Photopheresis step with an overnight incubation phase, prior to returning the treated cells to the patient. Transimmunization may be accomplished using a Photopheresis apparatus, although Transimmunization may also be accomplished without the use of a Photopheresis apparatus, using other methodology.

A controlled trial comparing conventional Photopheresis plus conventional immunosuppression with conventional immunosuppression alone in the prevention of rejection of transplanted hearts was recently published by Barr et al., Photopheresis for the prevention of rejection in cardiac transplantation, *New England Journal of Medicine*, Vol. 339, No. 4, 1744-51, Dec. 10, 1998. That study revealed that the addition of Photopheresis to the conventional immunosuppressive regimen quite significantly and safely reduced the number of rejection episodes, thereby markedly diminishing the need for dangerous boosting of the levels of toxic conventional immunosuppressive drugs. Similarly, in Greinix et al., Successful use of extracorporeal photochemotherapy in the treatment of severe acute and chronic graft-versus-host disease, *Blood*, Vol. 92, No. 9, 3098-3104, 1998, and in Greinix et al., Extracorporeal photochemotherapy in the treatment of severe steroid-refractory acute graft-versus-host disease: a pilot study, *Blood*, Vol. 96, No. 7, 2426-31, 2000, the authors describe testing which revealed that Photopheresis was particularly effective in reversing the adverse effects (known as graft-versus-host-disease or GVHD) following transplantation of bone marrow or stem cells.

One mechanism that is involved in the efficacy of Photopheresis has been recently deciphered. The flat plastic ultraviolet exposure system, a component of the Photopheresis apparatus, can cause the transformation of blood monocytes to dendritic antigen presenting cells (dendritic cells) as a result of the forces imposed on the monocytes as they flow past the plastic surface in a conventional Photopheresis apparatus. Since the therapeutic benefits resulting from the use of these dendritic cells are caused by the transfer of tissue antigens to dendritic cells capable of immunization of the patient against these antigens, the immunotherapy is referred to herein as "Transimmunization." Therefore, Transimmunization is a treatment that can, in one embodiment, be accomplished with a Photopheresis apparatus. Alternatively, the Transimmunization treatment may be performed using any other appropriate device having plastic channels which can induce differentiation of monocytes into dendritic cells. One important difference between the Transimmunization described herein and conventional Photopheresis is the recognition that the necessary tissue antigens can best be delivered to the new dendritic cells by overnight ex vivo incubation, prior to return to the patient of the loaded antigen dendritic cells.

In Photopheresis, a photoactivatable agent, such as 8 methoxypsoralen (8-MOP), is activated by exposure to ultraviolet A (UVA) in extracorporeally circulated blood, causing the 8-MOP to form photo adducts with pyrimidine bases of DNA and tyrosine containing cytoplasmic proteins. The positive clinical sequelae caused by Photopheresis result from the patient's immunologic response to the reinfused treated blood. The resulting immune response can, in the best responders, lead to the selective suppression or even elimination of the pathogenic clone(s).

As stated above, it has more recently been discovered that the passage of the blood through the plastic ultraviolet exposure chamber of the Photopheresis device can stimulate the conversion of blood monocytes to dendritic antigen presenting cells (DC), the most potent initiators of cellular immune reactions. The injured disease causing lymphocytes (either circulating malignant leukocytes or expanded populations of auto-reactive T cells) may be ingested by the newly formed DC, which then process and present the distinctive antigens of the pathogenic leukocytes to a responding immune system. The CD8 (and probably also CD4) T cell responses caused or enhanced by this treatment can often be sustained for long periods of time. The process has been used to maximize ingestion of apoptotic pathogenic T cells by newly formed DC.

Studies in an experimental model of conventional Photopheresis revealed the capacity of that treatment to selectively suppress rejection of transplanted tissue. Specifically, when skin was transplanted from a donor black mouse to a genetically distinct white mouse, the transplanted skin was completely rejected within 14 days. This was anticipated, since the donor and recipient mice differed in terms of histocompatibility antigens to a level equivalent to a six out six mismatch in humans and since skin is the most immunogenic solid organ. Following the rejection of the transplanted skin, the recipient mouse was sacrificed and its spleen, containing markedly expanded clones of those T cells causing the rejection, as well as tissue monocytes, were brought into single cell suspension. Then, in a system devised to mimic conventional photopheresis, the suspended T cells were exposed in a petri dish to UVA activated 8-MOP and then returned intravenously to a mouse genetically identical to the original recipient, thereby immunizing this new mouse against the clones of T cells involved in the rejection of the transplanted skin.

This new mouse then received new skin transplants: one from the same original donor strain and another from a third mouse strain completely unrelated to either of the other two strains. Instead of being rejected within 14 days as before, the transplanted skin from the original donor strain now survived intact for the full 42 days of the experiment. In contrast, the simultaneously transplanted skin from the third unrelated strain was rejected within the 14 days. The selective suppression of the rejection of the skin graft could be transferred to another set of mice, genetically identical to the original recipient, by transfusion of recipient T cells. These results demonstrated that the experimental model of Photopheresis led to donor specific suppression of the rejection of the transplanted skin and that this suppression was mediated by selectively suppressive T cells induced by the procedure. These tests are reported in more detail in Yamane et al., Suppression of anti-skin-allograft response by photodamaged effector cells—the modulating effects of prednisone and cyclophophamide, *Transplantation*, Vol. 54, 119-124, No. 1, July 1992; Perez et al., Induction of a cell-transferable suppression of alloreactivity by photodamaged lymphocytes, *Transplantation*, Vol. 54, 896-903, No. 5, November 1992; Perez et al., DNA associated with the cell membrane is involved in the inhibition of the skin rejection response induced by infusions of photodamaged alloreactive cells that mediate rejection of skin allograft, *Photochemistry and Photobiology*, Vol. 55, 839-849, No. 6, 1992.

Paradoxically, when the experiment was altered so that the donor strain differed from the recipient strain by only minor histocompatibility antigens, the transplanted skin could be kept intact on the recipient for only 21 days. This was longer than in untreated controls, but only half as long as when skin from the completely unrelated strain was transplanted to prepared recipients. Although puzzling at the time, it appears that the stronger the reaction that is being suppressed, the more effective it is. This is probably due to the preferential sensitivity of high affinity T cells, more readily generated by potent immune reactions, to be suppressed directly by the immature DC produced in the experimental Photopheresis procedure. Importantly, this finding suggests that the Transimmunization process described below may be most effective in preventing rejection of transplanted organs when the donor and recipient are mismatched by one or more HLA antigens. Accordingly, Transimmunization may dramatically augment the donor pool of transplantable tissue.

Cancer patients are often prepared for bone marrow/stem cell transplants from genetically distinct individuals by first receiving large doses of chemotherapy to accomplish two goals: diminution of the tumor burden and weakening of the immune system so that the transplanted cells will not be quickly rejected. This level of preparation is itself life threatening, since the cancer patient's own bone marrow is largely destroyed by the preparative chemotherapy. If the transplanted cells do not take and ultimately reconstitute the patient's bone marrow, the patient will succumb to infections, anemia, hemorrhage, etc. When the bone marrow/stem cell transplant does successfully reconstitute the patient's immune system, that immune system is repopulated by the cells of the donor. These donor cells then recognize the recipient's tissue as foreign and attack (reject) the recipient's own organs in a process called graft versus host disease (GVHD). Most prominently attacked in this resulting GVHD are the skin (which can slough), the liver (which can fail) and the intestinal tract (which can cease to function properly and hemorrhage). Life-saving reversal or suppression of GVHD is quite difficult with conventional treatments, which are usually quite toxic.

Remarkably, in recent years, it has become clear that a controllable level of GVHD may be of great benefit to the cancer patient. Since the donor cells react against recipient histocompatibility antigens, and since the residual cancer cells are also recipient cells bearing the patient's histocompatibility antigens, a certain level of "graft-versus-tumor" reaction or GVTR commonly accompanies the undesirable other components of GVHD. Those cancer patients who survive GVHD following bone marrow/stem cell transplants appear to have an improved survival from their cancer, since recurrences are less frequent. Therefore, a fine line exists between the toxic effects of GVHD and the beneficial ones of GVTR. In an ideal situation, a treatment could suppress GVHD while leaving a partial GVTR, directed at those weaker antigens which distinguish the malignant cells from the benign cells of the recipient. The possibility that Transimmunization can suppress GVHD while leaving the weaker GVTR intact is plausible and needs to be tested in humans, since the experiments indicate that Transimmunization may more effectively suppresses the strongest immune reactions, as discussed above.

SUMMARY OF THE INVENTION

The present invention provides methods to selectively immunosuppress the recipient of transplanted organs, tissue, bone marrow or stem cells, thereby enhancing the likelihood that the transplanted tissue or cells will be immunologically tolerated by the recipient. In one embodiment of the invention, which is particularly useful for organ or tissue transplants, a skin transplant is performed using skin from the intended organ donor and transplanting the skin to the intended organ recipient. After the recipient's immune system reacts to the transplanted skin, a quantity of the transplant recipient's blood is treated using Transimmunization to induce in the recipient T cells capable of suppressing immunologic rejection of subsequently transplanted tissue. The efficacy of the treatment can be verified, if desired, by performing sequential additional skin grafts to assess whether the recipient has been rendered sufficiently tolerant to the potential donor's tissues to permit tolerance of other organ(s) from the same donor.

In another embodiment of the invention for use in bone marrow or stem cell transplants, the method described above is used to suppress immunologic rejection of the transplant, and a reduced level of preparative (immunosuppressive) chemotherapy may be administered.

The method of the present invention also may be used to reduce the likelihood of graft versus host disease in bone marrow/stem cell transplant recipients, and may be especially useful when the donor and recipient are siblings sharing a set of parents. In this embodiment, the donor receives skin transplants from both of the sibling's parents, whose cells collectively express all of the tissue antigens of the recipient, including those not expressed by the sibling donor. After an immune response to the parental skin grafts is triggered in the donor, the Transimmunization procedure is performed on the donor. The treatment results in the donor being tolerized to the full range of histocompatibility antigens which may characterize the recipient's tissues. The donor bone marrow stem cells are then transplanted in combination with the donor's induced suppressor T cells to reduce the incidence or severity of GVHD in the recipient.

In another embodiment of the present invention, tumor loaded dendritic cells are injected intradermally to assess the level of anti-tumor immunity in a patient. Preferably, both the tumor cells and dendritic cells are from the particular patient and preferably, although not a requirement, the dendritic cells will have been produced by Transimmunization and then loaded with the patient's own apoptotic malignant cells. The level of the cancer patient's immune response against the relevant cancer antigens can be determined by measuring the amount of induration in the skin site injected, and the frequency of Transimmunization treatments can then be titrated to a desirable level. For example, when sufficient skin induration results, due to the infiltration of the skin test site by anti-tumor T cells, the patient's induced anti-tumor immunity will be considered acceptable and Transimmunization treatments can be withheld. Alternatively, when the skin induration at the test site is not sufficient, additional Transimmunization treatments to further boost the anti-tumor immunity can be administered.

One of the advantages of the methods of the present invention is that the use of globally immunosuppressive drugs in transplant recipients may be reduced or eliminated, thereby reducing or eliminating the adverse health effects associated with immunosuppressive drugs. Another advantage of the methods of the present invention is that the incidence and severity of GVHD in bone marrow/stem cell transplant recipients may be greatly reduced. A further advantage of the methods of the present invention is that the pool of potential transplant donors may be expanded. Other advantages of the methods of the present invention will be readily apparent to those skilled in the art based on the detailed description of preferred embodiments set forth below.

DETAILED DESCRIPTION OF PREFERRED EMBODIMENTS

The present invention relates to methods for using skin allografts to induce and measure selective suppression of the immune response in individuals, prior to their receiving transplanted organs, tissue, bone marrow or stem cells. The method involves the use of skin grafts to induce an immunological response in the donor or recipient, as desired, followed by a Transimmunization procedure. By inducing T cells capable of suppressing the rejection of allografted skin, the Transimmunization procedure also induces T cells capable of suppressing the immunologic rejection of subsequently transplanted tissue or cells expressing identical transplantation antigens. The Transimmunization procedure has been described for use in treatments involving cutaneous T-cell lymphoma or other disease effector agents in U.S. patent application Ser. Nos. 09/294,494 and 10/066,021, both titled "Methods for Inducing the Differentiation of Monocytes Into Functional Dendritic Cells and Immunotherapeutic Compositions Including Such Dendritic Cells", the entire contents of both of which are expressly incorporated herein by reference.

In a first embodiment of the method of the present invention, which may be especially useful in the case of organ or tissue transplantation, the intended recipient of the organ or tissue transplant is treated to enhance the likelihood that the transplanted organ or tissue will be immunologically tolerated by the recipient. A skin transplant is performed by removing a piece of skin from the intended organ or tissue donor, who may be either a living or cadaveric donor. The sequestered skin is then transplanted to the intended organ or tissue recipient. The skin transplant may be performed using standard skin grafting methods known to those skilled in the art. The size of the skin graft must be sufficient to induce an immunological response in the recipient, and typically need be no more than the size of a standard skin biopsy sample. In certain circumstances, it may be preferable to use a larger skin specimen, especially when the specimen is obtained from a cadaver donor. The skin may be transplanted to any part of the recipient's body, although it will typically be desirable to transplant the skin to an unexposed skin site, such as, for example, the buttocks.

Because the transplanted skin is incompatible with the recipient's tissue type, it will induce an immunologic response in the recipient and will ordinarily be rejected. Following the induction of the immunological response, the recipient's blood is treated using the Transimmunization process, as described in detail below. The Transimmunization procedure will typically be performed following rejection of the skin by the recipient, although the invention is not limited in this regard and the Transimmunization process may be performed at any time following or even preceding induction of the immunological response to the skin transplant in the donor.

As noted above, Transimmunization has been generally described previously. As used in the method of the present invention, the Transimmunization treatment results in the induction of T cells in the patient capable of suppressing the immunological response to the transplanted organ or tissue. The Transimmunization process is performed by obtaining an extracorporeal quantity of the subject's blood, treating the blood to induce differentiation of monocytes into immature dendritic cells, inducing apoptosis or necrosis of T cells in the blood, incubating the blood for a sufficient period of time to allow the dendritic cells to phagocytize the apoptotic T-cells, and administering the immature, antigen-loaded dendritic cells to the subject. Apoptosis, i.e. programmed cell death, leads to display on the surface of the dying cell of membrane molecules for which immature dendritic cells have receptors, thereby facilitating the ingestion of the dying cells (or their fragments) and the processing of their antigens by dendritic cells. Recently, it has become generally recognized that antigens of cells that die by routine necrosis (as well as their fragments) can also be internalized and processed by dendritic cells. Accordingly, it should be understood that the methods described herein can be performed using cells that have been rendered either apoptotic or necrotic.

It is often advantageous for the reintroduced dendritic cells to remain immature, in a state in which they preferentially induce immune suppression, rather than anti-allograft immune responses which can be produced by mature dendritic cells. Therefore, steps can be taken to prevent the dendritic cells from maturing. For example, it is well known in the field that exposure of the immature dendritic cells to appropriate doses of γ-irradiation will truncate the maturation of the dendritic cells, while still leaving them functional. Other approaches to keeping the dendritic cells immature, such as exposure to certain cytokines (e.g., IL-10), are also well known and could be substituted when appropriate for γ-irradiation.

If desired, two or more aliquots of the subject's blood may be taken and treated. A first aliquot is treated to induce monocyte differentiation, while a second aliquot is treated to induce apoptosis of T cells. The aliquots are combined after treatment and incubated together for a sufficient period of time to allow the dendritic cells to mature and phagocytize the apoptotic T cells. However, it will often be possible to simultaneously induce the monocyte-to-dendritic cell maturation and the apoptosis of the anti-allograft T cells.

Monocyte differentiation is initiated by exposing monocytes contained in an extracorporeal quantity of a subject's blood to physical perturbation, in particular to the forces exerted on the monocytes by their sequential adhesion to and release from plastic surfaces as they flow through a narrow plastic channel, such as the narrow plastic channel in a conventional Photopheresis device.

In a preferred embodiment of the invention, a white blood cell concentrate is prepared in accordance with standard leukapheresis practice using a leukapheresis/Photopheresis apparatus of the type well known to those skilled in the art. The white blood cell concentrate includes monocytes, lymphocytes and some red blood cells and platelets. Two billion white blood cells can typically be collected during leukapheresis. Assuming that monocytes comprise from about 2% to about 50% of the total white blood cell population collected, approximately 40 million to 1 billion monocytes are present in the white blood cell concentrate. The median monocyte percentage is approximately 20%, so commonly about 400 million monocytes will be in the white blood concentrate collected via leukapheresis.

Following separation by leukapheresis, monocyte differentiation is induced by pumping the blood cell concentrate through a device having a plurality of plastic channels. Preferably, the plastic channels have a diameter of between about 0.5 mm and 5.0 mm. Most preferably, a conventional Photopheresis apparatus having a channel diameter of 1 mm or less is used. The narrow channel configuration of the Photopheresis apparatus maximizes the surface area of plastic to which the blood cell concentrate is exposed as it flows through the Photopheresis apparatus. The invention is not limited in this regard, however, and any appropriate device having plastic channels may be used to induce monocyte differentiation.

While the invention is not limited to any particular mechanism of monocyte differentiation, it is believed that monocytes in the blood cell concentrate are attracted to the plastic channel walls of the Photopheresis apparatus, and the monocytes adhere to the channel walls. The fluid flow through the channel imposes shearing forces on the adhered monocytes that cause the transiently and incompletely adherent monocytes to be released from the plastic channel walls. Accordingly, as the monocytes pass through the Photopheresis apparatus, they may undergo numerous episodes of transient adherence to and release from the plastic channel walls. These physical forces send activation signals though the monocyte cell membrane, which results in induction of differentiation of monocytes into functional dendritic cells. Preliminary evidence suggests that interaction of monocyte β-glycoprotein with the plastic surface may contribute to the monocyte entry into the dendritic cell maturational pathway. Therefore, it may be possible to induce monocyte-to-dendritic cell maturation by direct interaction with monocyte P-glycoprotein, without use of a plastic flow system.

Inducing monocytes to form dendritic cells by the plastic transient adherence flow method offers several advantages for treatment related to organ or tissue transplants. Because all of the dendritic cells are formed from the monocytes within a very short period of time, the dendritic cells are all of approximately the same age. Dendritic cells will phagocytize apoptotic cells, such as apoptotic T cells, during a distinct period early in their life cycle. By creating dendritic cells with a relatively narrow age profile, the method of the present invention provides an enhanced number of immature dendritic cells capable of phagocitizing apoptotic T cells and subsequently presenting antigens from those T cells. Because immature dendritic cells are deficient in certain costimulatory surface molecules, such as those of the B7 family, they send suppressive signals to antigen-responsive T cells with which they develop cell-to-cell contact. Since the dendritic cells produced during the Transimmunization procedure are all the same age, this approach can provide an abundance of immature dendritic cells capable of producing dominant suppression of the otherwise potent immune reactions which can cause rejection of transplanted organs.

T cells contained in the extracorporeal quantity of blood may be rendered apoptotic or necrotic by any method known to those skilled in the art. For example, apoptosis may be induced by exposing the T cells to ultraviolet energy, x-ray irradiation or y-irradiation. Also, heat shock, cold shock, hydrostatic pressure or hypotonic solutions can lethally damage T cells or other cells in ways, such as cellular necrosis, that lead to their uptake and processing by dendritic cells, in analogous fashion that can also trigger the same immune phenomena. If desired, combinations of these methods may be used to render T cells apoptotic or necrotic.

There are two categories of apoptotic or necrotic cells which can be fed to immature dendritic cells to provide antigens which can contribute to the induction of allograft immunotolerance. These two sources of cells can by used independently or synergistically to produce the desired tolerance of the allografts.

The first category is comprised of those T cell clones capable of causing rejection of the organ transplant. In most clinical allograft rejection settings, there are numerous clones of T cells, each recognizing a distinct molecular component of the allografted cells, involved in the rejection phenomenon. Representative T cells from each of these clones can be rendered apoptotic or necrotic and fed to the immature dendritic cells to induce the desired tolerance of the allograft. The skin allografts, by simulating the immunologic situation typical of the actual organ transplant, leads to expansion of the anti-allograft T cell clones and therein provides a source of such T cells for the Transimmunization suppression of anti-allograft immunity.

A second category of apoptotic or necrotic cells which can be fed to the immature dendritic cells are cells from the organ donor. Easily accessible cell sources are blood leukocytes, or cultured cells (such as lymphocytes, keratinocytes, or other cells). These cells will contain antigens typical of the transplantable organs from the same individual donor. If such cells are rendered apoptotic or necrotic and fed to immature dendritic cells of the recipient, antigens typical of the donor will be displayed on the dendritic cell surface. Because the immature dendritic cells are deficient in costimulatory molecules, they will directly or indirectly (through immunoregulatory networks) inactivate recipient anti-allograft T cells after reinfusion into the recipient. This approach has the advantage of inactivating all clones of anti-allograft T cells.

Therefore, these two categories of apoptotic/necrotic cells can be use independently, or preferably, in tandem. For example, following skin allografting, the Photopheresis apparatus can be used to prepare anti-allograft T cells for loading into simultaneously induced immature dendritic cells. These two cell populations can be cultivated overnight to maximize cell contact and dendritic cell uptake of apoptotic anti-allograft T cells. Apoptotic donor leukocytes (or other donor cells) could be added to the overnight incubation, so that they would be processed by the same immature dendritic cells. Then the doubly loaded immature dendritic cells could be intravenously returned to the patient, to produced maximal immunologic tolerance of the allograft. This tolerance could be assessed using a repeat skin allograft from the same donor.

In one embodiment of the present invention, T cells in the extracorporeal quantity of the recipient's blood are rendered apoptotic in the Photopheresis apparatus as the monocytes are induced to form dendritic cells by the physical forces they experience as they flow through the narrow plastic channels in the Photopheresis apparatus. A photoactivatable agent capable of inducing apoptosis in the T cells is added to the blood cell concentrate prior to passage through the Photopheresis apparatus, and the blood cell concentrate is irradiated as it passes through the Photopheresis apparatus to render the T cells apoptotic. By rendering the T cells apoptotic in the Photopheresis apparatus, these cells are immediately available to be phagocytized as the monocytes are differentiating to form dendritic cells.

In this embodiment of the present invention, saline is added to the white blood concentrate prior to passage through the Photopheresis apparatus to dilute the red blood cell concentration to about 2% by volume, thereby permitting more effective penetration of the activating radiation to the target T cells. The photoactivatable agent can be administered to the subject prior to obtaining a quantity of blood from the subject for leukapheresis and Photopheresis. Alternatively, or additionally, the photoactivatable agent can be added directly to the extracorporeal bloodstream, typically by injecting the agent into the tubing leading to the leukapheresis/Photopheresis apparatus. Regardless of when and how a particular agent is administered, the T cells must be exposed to the photoactivatable agent for a period of time sufficient for the agent to react with cellular components in the disease cells.

Exemplary photoactivatable agents are psoralens, porphyrins, pyrenes, phthalocyanine, retinoid derivatives, photoactivated cortisone, photoactivated antibodies specifically reactive with the monocytes, photactivatable dyes, and monoclonal antibodies which have been linked to porphyrin molecules.

The psoralens are a preferred class of photoactivatable agents for use in the Photopheresis procedure. Psoralens are readily absorbed from the digestive track, reaching peak levels in the blood and other tissues in one to four hours following oral administration, and these agents are excreted almost entirely within 24 hours. Accordingly, the psoralens are particularly suitable for oral administration prior to obtaining an extracorporeal quantity of the subject's blood. The psoralen molecules are inert prior to exposure to irradiation and are transiently activated to an excited state following irradiation. The transiently activated psoralen molecules are capable of forming photoadducts with cellular DNA, proteins or lipids and generating other reactive species, such as singlet oxygen, which are capable of modifying other cellular components, e.g., the cell membrane and cytoplasmic components such as proteins and aromatic amino acids.

The preferred psoralens include 8-methoxypsoralen (8-MOP), 4' aminomethyl-4, 5', 8 trimethyl-psoralen (AMT), 5-methoxypsoralen (5-MOP), and trimethyl-psoralen (TMP). 8-MOP is the most preferred photoactivatable agent for use with the methods of the invention, and the conditions for oral administration of this psoralen are described in U.S. Pat. No. 5,147,289, the disclosure of which is incorporated herein by reference.

The irradiation stage of Photopheresis is performed by passing the monocyte/lymphocyte fraction through an exposure device which may be contained within the leukapheresis/Photopheresis apparatus or may be physically separate. The preferred exposure device includes a transparent plastic channel having a diameter of about 1 mm disposed between opposed irradiation sources. As the monocyte/lymphocyte fraction passes through the channel, the T cells are never separated from the irradiation sources by more than about 0.5 mm of blood. Maintaining the T cells in such close proximity to the irradiation sources has proven particularly effective in ensuring adequate exposure of the lymphocyte fraction to the activating radiation. In the case where a psoralen such as 8-MOP is used as the photoactivatable agent, the irradiation sources emit ultraviolet A radiation (UVA) as the activating radiation. To activate the psoralen, the monocytes are typically exposed to about 1-2 joules/cm2 of UVA for a period of from about 15 to about 150 minutes.

Following treatment of the blood to initiate differentiation of monocytes and to render T cells in the blood apoptotic, the treated blood cell concentrate is sequestered for incubation in the presence of apoptotic T cells obtained from the intended transplant recipient. The incubation period allows the dendritic cells forming and maturing in the blood concentrate to be in relatively close proximity to the apoptotic T cells, thereby increasing the likelihood that the apoptotic T cells will be consumed and processed by the dendritic cells. As described above, the T cells may be induced to undergo apoptosis as the blood concentrate is being passed through the Photopheresis apparatus. However, apoptosis of T cells under these circumstances does not typically become evident until at least twelve hours have elapsed from the time of the ultraviolet exposure. Since the uptake of damaged leukocytes by immature dendritic cells efficiently occurs only after apoptosis becomes evident, optimally an incubation phase is incorporated (prior to return of cells to the patient) of at least 12 hours to permit efficient cellular uptake by the DC. Alternatively, the T cells may be treated separately to induce apoptosis and added to the blood concentrate before or after passage of the blood concentrate through the Photopheresis device.

A standard blood bag may be utilized for incubation of the cells, as is typical in Photopheresis. However, it has been found to be particularly advantageous to use a blood bag of the type which does not leach substantial amounts of plasticizer and which is sufficiently porous to permit exchange of gases, particularly $CO_2$ and $O_2$. Such bags are available from, for example, the Fenwall division of Baxter Healthcare Corp. under the name Amicus* Apheresis Kit. Various plasticizer-free blood bags are also disclosed in U.S. Pat. Nos. 5,686,768 and 5,167,657.

The blood cell concentrate and apoptotic T cells are incubated for a period of time sufficient to maximize the number of functional antigen presenting dendritic cells in the incubated cell population. Incubation is performed under conditions known to those skilled in the art. An exemplary incubation protocol is described in U.S. patent application Ser. No. 10/066,021, the entire contents of which are incorporated herein by reference. Typically, the treated blood cell concentrate and T cells are incubated for a period of from about 6 to about 48 hours, with the preferred incubation time extending over a period of from about 12 to about 24 hours. By treating monocytes in the manner described above and then incubating the treated cell population, a large number of functional antigen presenting dendritic cells can be obtained. It has been found to be particularly advantageous to add a buffered culture medium to the blood bag and one or more cytokines, such as GM-CSF and IL-4, during the incubation period.

The large numbers of functional dendritic cells generated during incubation provide a ready means of presenting selected antigens from T cell clones involved in the immunologic response to the donor's skin grafted on the intended transplant recipient. Bringing mature dendritic cells into close contact with such apoptotic T cells within the confines of the blood bag provides large numbers of dendritic cells loaded with antigens from the T cell clones. The antigen-loaded dendritic cells can be used as immunogens by reinfusing the cells into the subject or by otherwise administering the cells in accordance with methods known to elicit an immune response, such as subcutaneous, intradermal or intramuscular injection. The antigen loaded dendritic cells induce the production of T cells, referred to herein as "suppressor T cells", that act to suppress the action of the T cell clones in the recipient that were responsible for the immunologic rejection of the transplanted skin graft. Because the suppressor T cells specifically, or preferentially, suppress only the T cell clones that attack the transplanted organ or tissue, immunological rejection of the organ or tissue can reduced or eliminated. By suppressing the action of the T cells responsible for immunologic rejection, the transplanted tissue can be tolerated by the recipient with lower doses of immunosuppressive drugs.

The efficacy of the Transimmunization treatment described above in reducing the recipient's immunologic response can be tested prior to organ transplantation, if desired, by performing a second skin transplant on the recipient with skin from the donor to determine whether the recipient is more tolerant of the allografted skin. In this manner, the second, or subsequent, skin allograft is a safe surrogate marker for rejection. If the recipient is acceptably tolerant of the transplanted skin, as determined in the professional judgment of the physician based upon consideration of factors such as length of survival and examination of the transplanted skin, the recipient may be ready to receive the transplanted organ or tissue. If the recipient is not acceptably tolerant of the transplanted skin, additional skin transplants can be performed and the Transimmunization procedure described above can be repeated until a skin transplant from the donor is acceptably tolerated.

As will be apparent to one of skill in the art, the method of the present invention can be used in combination with immunosuppressive drugs as may be appropriate. The need for or dosage of immunosuppressive drugs may be reduced or eliminated as a result of the treatment, thereby reducing the recipient's susceptibility to infection or disease, or other adverse effects associated with the use of immunosuppressive drugs.

In another embodiment of the present invention, which is especially useful for bone marrow or stem cell transplantation, the transplant recipient can be made more tolerant of the transplant donor cells, thereby reducing the amount of preparative chemotherapy required. In this embodiment of the invention, the recipient receives a skin graft from the donor, and the Transimmunization procedure is performed as described above using blood obtained from the recipient. Testing can be performed prior to introduction of the bone marrow or stem cells by using additional skin grafts to determine if the recipient is sufficiently tolerant of the donor's skin graft. If desired, the recipient may be administered a level of preparative chemotherapy that is sufficient in combination with the Transimmunization treatment to induce an acceptable tolerance of a skin graft from the donor. When the recipient's tolerance for a skin graft from the donor is acceptable in the judgment of the physician, thereby diminishing the likelihood that the donor cells will be rejected, the bone marrow or stem cell transplant is performed.

By increasing the recipient's tolerance for the donor's bone marrow or stem cells, preparative ablative chemotherapy can be minimized, thereby reducing the adverse effects that may occur as a result of preparative chemotherapy. This treatment may also enhance the capacity of the transplanted bone marrow or stem cells to establish themselves in the recipient. Moreover, by rendering the recipient more tolerant of the donor cells prior to transplantation, the donor pool may be expanded to include potential donors with less than a six out of six match of the major histocompatibility complexes.

In another embodiment of the present invention, which is especially useful in bone marrow or stem cell transplantation, immunologic suppressor T cells are induced in the donor and transplanted with the donor's bone marrow or stem cells. In this embodiment of the invention, the bone marrow/stem cell donor receives skin transplants from each of the two parents of the intended recipient of the bone marrow/stem cell transplant. When an immunologic response to the skin grafts is generated in the donor, a quantity of the donor's blood is subjected to Transimmunization as described above. Because the cells of the two parents produce and display all of the histocompatibility antigens present in the recipient, suppressor T cells will be induced in the donor for the full range of tissue antigens of both parents. If desired, repetitive skin grafts from the recipient's parents can be performed until an acceptable level of survival of the transplanted skin is achieved.

After an acceptable level of survival of transplanted skin is achieved, a combination of bone marrow/stem cells and induced suppressor T cells from the donor are transplanted to the recipient. The donor stem cells will broadly reconstitute the recipient's immune system, as well as initiate a potentially beneficial graft-versus-tumor reaction. The donor suppressor T cells will inhibit undesirable graft-versus-host disease. By making the donor more tolerant of the recipient's histocompatibility antigens prior to transplantation, the chance of life-threatening GVHD will be minimized, and the donor pool can be expanded.

Where the bone marrow/stem cell donor is a parent of the intended recipient, the method described above is modified in that the parent donor will receive a skin graft only from the non-donor parent, and the Photopheresis/Transimmunization treatment as described above is performed. The skin graft from the non-donor parent will sensitize the donor parent to antigens that the recipient may have inherited from the non-donor parent, resulting in suppressor T cells for the full range of histocompatibility antigens in the recipient. When the Photopheresis/Transimmunization procedure has been completed in the donor parent, a combination of bone marrow/stem cells and induced suppressor T cells from the donor parent are transplanted to the recipient.

The present invention also provides a method for skin testing which may be performed to assess the level of anti-tumor immunity achieved in a patient treated with dendritic cells loaded with tumor antigens. The production and certain methods of use of tumor loaded dendritic cells has been described previously in U.S. patent application Ser. No. 09/294,494 titled "Methods for Inducing the Differentiation of Monocytes Into Functional Dendritic Cells and Immunotherapeutic Compositions Including Such Dendritic Cells," which is expressly incorporated herein by reference in its entirety.

An aliquot of antigen presenting dendritic cells created by the method described in U.S. patent application Ser. No. 09/294,494 is injected intradermally in any acceptable skin location. The level of immune response against the cancer antigens presented by the dendritic cells is determined by measuring the amount of induration (i.e., tissue swelling) that occurs at the injection site. By measuring and following the level of induration occurring over a specified time period, typically between 48 hours and one week, the frequency of Photopheresis/Transimmunization treatments can be titrated to a desirable level to maximize the patient's anti-tumor immunity. In addition, because intradermal injections of tumor antigen loaded dendritic cells can serve as a boost of anti-tumor immunity in the patient, the testing method described above can be used to determine the appropriate number and frequency of intradermal antigen loaded dendritic cell booster shots.

I claim:

1. A method for selectively suppressing the immune response of an intended transplant recipient receiving a transplantation of bone marrow or stem cells, comprising the steps of:
    (a) removing a piece of skin from each of the two biological parents of the intended transplant recipient of the bone marrow or stem cell transplantation;
    (b) allografting the skin from each of the biological parents to the donor of the bone marrow or stem cells to be transplanted;
    (c) monitoring the donor to determine when an immunological response to the allografted skin occurs in the donor and obtaining a quantity of blood for treatment after an immunological response is observed;
    (d) treating an extracorporeal quantity of blood from the donor to induce at least one of apoptosis or necrosis of T cells present in the extracorporeal quantity of blood;
    (e) treating the extracorporeal quantity of blood from the donor by flowing the blood through an apparatus having plastic channels having a diameter of between about 0.5 mm and 5.0 mm;
    (f) incubating the extracorporeal quantity of blood; and
    (g) administering the extracorporeal quantity of blood to the intended transplant recipient.

2. The method of claim 1, wherein apoptosis of T cells in the extracorporeal quantity of blood is induced by adding a photoactivatable agent to the extracorporeal quantity of blood, and irradiating the extracorporeal quantity of blood.

3. The method of claim 2, wherein the photoactivatable agent is 8-MOP.

4. The method of claim 1, wherein the apoptosis or necrosis of T cells in the extracorporeal quantity of blood is induced by treating the blood using a treatment selected from the group consisting of heat shock, ultraviolet radiation, cold shock, x-ray irradiation, gamma irradiation, hydrostatic pressure and hypotonic solutions.

5. The method of claim 1, wherein the extracorporeal quantity of blood is incubated for a period of from about 6 to about 48 hours.

6. The method of claim 5, wherein the extracorporeal quantity of blood is incubated for a period of from about 12 to about 24 hours.

7. The method of claim 2, wherein the steps of irradiating the extracorporeal quantity of blood and of treating the extracorporeal quantity of blood by flowing the blood through an apparatus having plastic channels are performed in a Photopheresis apparatus.

8. The method of claim 1, wherein the extracorporeal quantity of blood is treated by flowing the blood through an apparatus having plastic channels with a diameter of about 1 mm or less.

9. A method for selectively suppressing the immune response of an intended transplant recipient receiving a transplantation of bone marrow or stem cells, comprising the steps of:
    (a) removing a piece of skin from each of the two biological parents of the intended transplant recipient of the bone marrow or stem cell transplantation;
    (b) allografting the skin from each of the biological parents to the donor of the bone marrow or stem cells to be transplanted;
    (c) monitoring the donor to determine when an immunological response to the allografted skin occurs in the donor and obtaining a quantity of blood for treatment after an immunological response is observed;
    (d) separating monocytes and T-cells from the extracorporeal quantity of the donor's blood by subjecting the blood to a leukapheresis process;
    (e) treating the separated T-cells to induce at least one of apoptosis or necrosis of the T cells;
    (f) treating the separated monocytes from the donor by flowing the blood through an apparatus having plastic channels having a diameter of between about 0.5 mm and 5.0 mm;
    (g) combining the treated T cells and treated monocytes and incubating the combined cells; and
    (h) administering the extracorporeal quantity of blood to the intended transplant recipient.

* * * * *